United States Patent
Baum et al.

(10) Patent No.: US 6,504,015 B2
(45) Date of Patent: Jan. 7, 2003

(54) TETRAHYDROFURAN-ADDUCTED GROUP II β-DIKETONATE COMPLEXES AS SOURCE REAGENTS FOR CHEMICAL VAPOR DEPOSITION

(75) Inventors: Thomas H. Baum, New Fairfield, CT (US); Witold Paw, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/791,005

(22) Filed: Feb. 22, 2001

(65) Prior Publication Data

US 2001/0007034 A1 Jul. 5, 2001

Related U.S. Application Data

(62) Division of application No. 09/321,637, filed on May 28, 1999, now Pat. No. 6,218,518, which is a continuation-in-part of application No. 08/990,943, filed on Dec. 15, 1997, now Pat. No. 6,126,996, which is a division of application No. 08/477,797, filed on Jun. 7, 1995, now Pat. No. 5,840,897, which is a continuation-in-part of application No. 08/181,800, filed on Jan. 18, 1994, now Pat. No. 5,453,494, which is a continuation-in-part of application No. 07/918,141, filed on Jul. 22, 1992, now Pat. No. 5,280,012, which is a continuation of application No. 07/615,303, filed on Nov. 19, 1990, now abandoned, which is a division of application No. 07/581,631, filed on Sep. 12, 1990, now Pat. No. 5,225,561, which is a continuation-in-part of application No. 07/549,389, filed on Jul. 6, 1990, now abandoned, application No. 08/990,943, which is a continuation-in-part of application No. 08/414,504, filed on Mar. 31, 1995, now Pat. No. 5,820,664, which is a continuation-in-part of application No. 08/280,143, filed on Jul. 25, 1994, now Pat. No. 5,536,323, which is a continuation of application No. 07/927,134, filed on Aug. 7, 1992, now abandoned, which is a continuation-in-part of application No. 07/807,807, filed on Dec. 13, 1991, now Pat. No. 5,204,314, which is a continuation of application No. 07/549,389, filed on Jul. 6, 1990, now abandoned.

(51) Int. Cl.$^7$ ............................................. C07F 5/00
(52) U.S. Cl. ...................................... 534/15; 427/252
(58) Field of Search ............................. 534/7, 10–16; 427/252, 255.2, 255.32; 546/463, 510, 511, 512; 568/412, 615, 677; 505/100, 120, 121, 124, 125; 556/40, 42, 57, 136; 549/3, 206

(56) References Cited

U.S. PATENT DOCUMENTS

| | | | | |
|---|---|---|---|---|
| 5,204,314 A | * | 4/1993 | Kirlin et al. | 505/1 |
| 5,225,561 A | * | 7/1993 | Kirlin et al. | 546/256 |
| 5,248,787 A | | 9/1993 | Timmer et al. | |
| 5,280,012 A | * | 1/1994 | Kirlin et al. | 505/1 |
| 5,453,494 A | * | 9/1995 | Kirlin et al. | 534/15 |
| 5,536,323 A | * | 7/1996 | Kirlin et al. | 118/726 |
| 5,820,664 A | * | 10/1998 | Gardiner et al. | 106/287.17 |
| 5,840,897 A | * | 11/1998 | Kirlin et al. | 546/2 |
| 6,126,996 A | * | 10/2000 | Kirlin et al. | 427/252 |
| 6,218,518 B1 | * | 4/2001 | Baum et al. | 534/15 |

FOREIGN PATENT DOCUMENTS

| | | | | |
|---|---|---|---|---|
| JP | Hei 05-132776 | * | 5/1993 | C23C/16/18 |
| JP | 10-324970 | * | 12/1998 | C23C/16/18 |

* cited by examiner

*Primary Examiner*—Dameron L. Jones
(74) *Attorney, Agent, or Firm*—Margaret Chappuis

(57) ABSTRACT

Group II metal MOCVD precursor compositions are described having utility for MOCVD of the corresponding Group II metal-containing films. The complexes are Group II metal β-diketonate adducts of the formula $M(\beta\text{-diketonate})_2(L)_4$ wherein M is the Group II metal and L is tetrahydrofuran. Such source reagent complexes of barium and strontium are usefully employed in the formation of barium strontium titanate and other Group II thin films on substrates for microelectronic device applications, such as integrated circuits, ferroelectric memories, switches, radiation detectors, thin-film capacitors, microelectromechanical structures (MEMS) and holographic storage media.

12 Claims, 4 Drawing Sheets

TETRAHYDROFURAN-ADDUCTED GROUP II β-DIKETONATE COMPLEXES AS SOURCE REAGENTS FOR CHEMICAL VAPOR DEPOSITION

CROSS-REFERENCE TO RELATED APPLICATIONS

This is a division of U.S. application Ser. No. 09/321,637 filed May, 28, 1999, and issued Apr. 17, 2001 as U.S. Pat. No. 6,218,518, which is a continuation-in-part of U.S. patent application Ser. No. 08/990,943 filed Dec. 15, 1997, and issued Oct. 3, 2000 as U.S. Pat. No. 6,126,996, which is a division of U.S. patent application Ser. No. 08/477,797 filed Jun. 7, 1995, and issued Nov. 24, 1998 as U.S. Pat. No. 5,840,897, which is a continuation-in-part of U.S. application Ser. No. 08/181,800 filed Jan. 18, 1994, and issued Sep. 26, 1995 as U.S. Pat. No. 5,453,494, which is a continuation-in-part of U.S. application Ser. No. 07/918,141 filed Jul. 22, 1992, and issued Jan. 18, 1994 as U.S. Pat. No. 5,280,012, which in turn is a continuation of U.S. application Ser. No. 07/615,303 filed Nov. 19, 1990, now abandoned, which in turn is a divisional of U.S. application Ser. No. 07/581,631 filed Sep. 12, 1990, and issued Jul. 6, 1993 as U.S. Pat. No. 5,225,561, which in turn is a continuation-in-part of U.S. application Ser. No. 07/549,389 filed Jul. 6, 1990, now abandoned.

U.S. patent application Ser. No. 08/990,943 is also a continuation-in-part of U.S. application Ser. No. 08/414,504 filed Mar. 31, 1995, and issued Oct. 13, 1998 as U.S. Pat. No. 5,820,664, which in turn is a continuation-in-part of U.S. application Ser. No. 08/280,143 filed Jul. 25, 1994, and issued Jul. 16, 1996 as U.S. Pat. No. 5,536,323, which is a continuation of U.S. patent application Ser. No. 07/927,134, now abandoned, filed Aug. 7, 1992, which is in turn a continuation-in-part of U.S. patent application Ser. No. 07/807,807, filed Dec. 13, 1991, and issued Apr. 23, 1993 as U.S. Pat. No. 5,204,314, which is a continuation of U.S. patent application Ser. No. 07/549,389, filed Jul. 6, 1990, now abandoned.

The disclosures of all of the above-identified patent applications and appertaining patents are hereby incorporated herein by reference in their entireties. Priority to the above applications is hereby claimed under the provisions of 35 USC §120.

BACKGROUND OF THE INVENTION

1. Field of the Invention

The present invention generally relates to thermally decomposable organometallic source reagents that are useful in chemical vapor deposition (CVD) processes, for the formation of metal films on substrates. More specifically, the invention relates to Group II β-diketonate tetrahydrofuran complex source reagents useful for liquid delivery chemical vapor deposition of Group II metal-containing films.

2. Description of the Related Art

Chemical vapor deposition is widely used for the formation of metal films and/or metal containing films on a variety of substrates. CVD is a particularly attractive method for forming metal films because it is readily scaled up to production runs and because the electronics industry has a wide experience and an established equipment base in the use of CVD technology which can be applied to CVD processes.

CVD requires source reagents that are sufficiently volatile to permit their gas phase transport into the decomposition reactor. The source reagent must decompose in the CVD reactor to deposit only the desired element(s) at the desired growth temperature on the substrate. Premature gas phase reactions are desirably avoided, and it generally is desired to controllably deliver source reagents into the CVD reactor to effect correspondingly close control of film stoichiometry.

Many potentially useful metals do not form compounds that are well suited for CVD. Although some source reagents are solids that are amenable to sublimation for gas-phase transport into the CVD reactor, the sublimation temperature may be very close to the decomposition temperature. Accordingly, the reagent may begin to decompose in the lines leading to the CVD reactor, and it then becomes difficult to control the stoichiometry of the deposited films.

Accordingly, there is a continuing search in the art for improved source reagent compositions which are more amenable to vaporization to form the source component vapor for CVD processes, for applications such as the formation of diffusion barriers, conductors, dielectrics, protective coatings, phosphors, electroluminescent structures, ferroelectrics, giant magnetoresistive films, corrosion-resistant films, and mixed metal films.

In the chemical vapor deposition of multicomponent material systems, multiple source reagents are delivered to the CVD reactor. A particularly advantageous way of delivering multiple source reagents is to accurately mix neat liquid source reagents or liquid solutions of source reagents and then flash vaporize the mixture and deliver the resulting vapor to the reactor for deposition of metal components on a substrate heated to an appropriate temperature (liquid delivery metalorganic chemical vapor deposition). It is possible in this situation for the reagents to undergo reactions, either in the liquid phase before vaporization or in the gas phase after vaporization. If these reactions convert a source reagent to an insoluble or non-volatile product, or to a material of different chemical or physical properties, then the elements contained in that product will not reach the substrate and the stoichiometry of the deposited film will be incorrect.

Examples of this problem (wherein Et is ethyl; tBu is tert-butyl; iPr is isopropyl; and thd is tetramethylheptanedionate) include the following:

(i) during deposition of $PbZr_xTi_{1-x}O_3$, using $(Et)_4Pb$, $Zr(OtBu)_4$, and $Ti(OiPr)_4$ source reagents, ligand exchange between the Zr and Ti reagents resulted in formation of $Zr(OiPr)_4$ (and perhaps other products of which $Zr(OiPr)_4$ is a monomer), which had very low volatility and which condensed in the gas manifold or vaporizer;

(ii) when solutions of $Ba(thd)_2$ and $Ti(OiPr)_4$ were mixed prior to vaporization, an insoluble precipitate was formed, presumably $Ba(OiPr)_2$ or the mixed alcoxide β-diketonate of Ti, $Ti(OiPr)_2(thd)_2$, was found; and (iii) when solutions of $Pb(thd)_2$ and $Ti(OiPr)_4$ were mixed in butyl acetate, the reagents reacted to form compounds of differing physical properties, such as $Pb(OiPr)_2$ and $Ti(OiPr)_2(thd)_2$.

Another specific example illustrating this problem is the preparation of films of strontium bismuth tantalate and strontium bismuth niobate ($SrBi_2Ta_2O_9$ and $SrBi_2Nb_2O_9$) by CVD for use in non-volatile ferroelectric random access memories. The most commonly used strontium source reagents are β-diketonate complexes such as $Sr(thd)_2$. When a solution is heated containing the following source reagents for deposition of $SrBi_2Ta_2O_9$:

$Sr(thd)_2$; $Ta(OEt)_5$; and $Bi(Ph)_3$ wherein Ph=phenyl, the ethoxide ligands of the tantalum reagent exchange with the thd ligands of the strontium reagent, leading to the formation of undesirable strontium alkoxide species that have reduced volatility and that can decompose in the vaporization zone. Alternatively, when these reagents are provided separately in bubblers, similar ligand exchange reactions occur in the gas phase; the resulting solids constrict the gas lines, alter the film stoichiometry, and/or lead to the formation of particles in the films.

In certain instances, such problems can be avoided by using identical ligands on the metals to make ligand exchange a degenerate reaction (i.e., where the exchanging ligand is identical to the original ligand). Examples of this approach include the use of tetraethylorthosilicate, triethylborate and triethylphosphite for deposition of borophosphosilicate glasses (*J. Electrochem. Soc.*, 1987, 134(2), 430). In many instances, however, this method for avoiding the problem is not possible because the appropriate compound does not exist, is too unstable or involatile to be used for CVD, or otherwise has disadvantageous physicochemical material properties. For example, for deposition of $PbZr_xTi_{1-x}O_3$, a reagent system with identical ligands is problematic because while $Pb(thd)_2$ and $Zr(thd)_4$ are stable and volatile, $Ti(thd)_4$ does not exist and $Ti(thd)_3$ is extremely air sensitive. Similarly, while $Ti(OtBu)_4$ and $Zr(OtBu)_4$ are stable and volatile, $Pb(OtBu)_2$ is oligomeric and thermally unstable at temperatures required for volatilization.

The foregoing problems are also encountered in the circumstance where the metal source reagent is provided in a liquid solution and the solvent contains moieties that react with ligands of the source reagent compound to produce undesirable ligand exchange reaction by-products that display different physical properties and are involatile or insoluble in organic solvents.

As a result of interest in barium and/or strontium-based oxide thin films having desirable electrical properties, including barium strontium titanate (BST) as a dielectric thin film material, and strontium bismuth tantalate (SBT) as a ferroelectric thin film material, corresponding interest has been focused on liquid delivery MOCVD precursor source reagents for barium and/or strontium.

In this effort of developing new and improved Ba and Sr metalorganic precursors for the thin-film deposition of barium and/or strontium, the main focus of recent research efforts has been directed towards the formation of liquid complexes of Ba and Sr, since the existing precursors for these metals are believed to cause particle formation, resulting in vaporizer or delivery tube clogging and particles in the deposited films. As a result, such existing Ba and/or Sr precursors do not fully satisfy the requirements of the CVD process. Due to the nature of the liquid delivery MOCVD process, however, changes in both the Ba and Sr precursor chemistry are required.

In liquid delivery process applications in which solvent is employed to form a precursor composition, the solvent is often overlooked as a critical chemistry component. However, the solvent is exceedingly important with respect to the delivery and vaporization phenomena, being a major constituent of the chemical solution forming the source reagent composition in such instances, e.g., where the source reagent compound or complex is not utilized as a neat liquid, but rather is dissolved or suspended in a suitable and chemically compatible solvent medium (single- or multi-component).

Designing Group II liquid or low melting point solid CVD precursors represents a significant challenge. For example, the difficulties in obtaining suitable barium source reagent complexes stem from the highly electropositive character of barium, with its large ionic radius. The latter requires high coordination numbers that have to be satisfied by mostly neutral ligands. These ligands cannot coordinate strongly to the electropositive Ba center. As a result, barium CVD precursors are frequently characterized by insufficient thermal stability.

The lability of metal-ligand bonds in barium-based metalorganic compositions coupled with the large size of the metal center result in a tendency to aggregate to form multinuclear species. This can happen either during synthesis or transport, affecting the precursor volatility, or during the CVD process, lowering the transport rate and film growth efficiency. Formation of multinuclear species results in decreased solubility that can have critical impact on the nature and efficiency of the liquid delivery CVD process and may lead to particle formation in thin film growth.

In an actual approach to such precursor design issues, attempts should be made to achieve a best compromise between the basic requirements of stability, volatility and solubility, and particularly between stability and volatility. Previous work has shown that it is difficult to form very stable and simultaneously highly volatile complexes of Ba and Sr, however an appropriate compromised balance of stability and volatility for a given precursor may be utilized to provide an improved CVD process.

Previous film growth research has indicated that barium metalorganic CVD precursors are desirably (a) mononuclear metalorganic complexes, (b) soluble in organic solvents, such as aliphatic hydrocarbons, and (c) fluorine-free. The desired volatility of the complex may be achieved by using appropriate ligands species and limiting inter-nuclear interactions. This is especially critical for large electropositive metal centers such as barium.

As a result of the foregoing, interest in liquid sources of Group II (Ba, Sr, Ca, Mg) precursors has increased, both as a means for reducing the formation of solid particles during the liquid delivery process, and as a means for achieving improved vaporization characteristics. Due to the relatively large radii of the Group II elements, adducts become essential for forming mononuclear species possessing efficient vaporization and gas-phase transport characteristics.

Accordingly, it is an object of the present invention to provide improved Group II metal source reagent compositions for forming corresponding Group II metal-containing films via liquid delivery CVD processes.

It is another object of the invention to provide an improved method of liquid delivery metalorganic chemical vapor deposition utilizing such precursors.

Other objects and advantages of the invention will be more fully apparent from the ensuing disclosure and appended claims.

SUMMARY OF THE INVENTION

The present invention relates in one aspect to a Group II metal β-diketonate adduct of the formula $M(\beta\text{-diketonate})_2 (L)_4$ wherein M is a Group II metal and L is tetrahydrofuran. The Group II metal may be Mg, Ca, Sr, or Ba and the β-diketonate ligands may include at least one ligand selected from acac, thd, fod, tfacac, and hfacac, and their corresponding nitrogen and thio analogs.

The invention relates in another aspect to a barium bis (2,2,6,6-tetramethyl-3,5-heptanedionate) tetrakis (tetrahydrofuran) adduct having a melting point of about 25° C.

A further aspect of the invention relates to a strontium bis (2,2,6,6-tetramethyl-3,5-heptanedionate) tetrakis (tetrahydrofuran) adduct having a melting point of about 30° C.

Another compositional aspect of the invention relates to a barium (β-diketonate) tetrakis (tetrahydrofuran) adduct having the ORTEP diagram structure illustrated in FIG. 3 hereof.

Yet another compositional aspect of the invention relates to a strontium (β-diketonate) tetrakis (tetrahydrofuran) adduct having the ORTEP diagram structure illustrated in FIG. 4 hereof.

In a further aspect, the invention relates to a Group II metal source reagent solution comprising a tetrahydrofuran solution of a Group II metal β-diketonate adduct of the formula M(β-diketonate)$_2$(L)$_4$ wherein M is a Group II metal and L is tetrahydrofuran.

Other compositional aspects of the invention variously relate to:

a Group II metal source reagent solution comprising a tetrahydrofuran solution of a barium bis (2,2,6,6-tetramethyl-3,5-heptanedionate) tetrahydrofuran adduct having a melting point of about 25° C.;

a Group II metal source reagent solution comprising a tetrahydrofuran solution of a strontium bis (2,2,6,6-tetramethyl-3,5-heptanedionate) tetrahydrofuran adduct having a melting point of about 30 °C.;

a Group II metal source reagent solution comprising a tetrahydrofuran solution of a barium bis (2,2,6,6-tetramethyl-3,5-heptanedionate) tetrahydrofuran adduct having the ORTEP diagram structure illustrated in FIG. 3 hereof; and a Group II metal source reagent solution comprising a tetrahydrofuran solution of a strontium bis (2,2,6,6-tetramethyl-3,5-heptanedionate) tetrahydrofuran adduct having the ORTEP diagram structure illustrated in FIG. 4 hereof.

It is to be appreciated that the compositions disclosed herein, in respect of constituent components and/or moieties of such compositions, may variously, selectively and independently "comprise," "consist," or "consist essentially of," such constituent component(s) and/or moiet(y/ies).

In another aspect, the present invention relates to a method of forming a Group II metal-containing film on a substrate, comprising the steps of:

providing a liquid delivery apparatus including a vaporizer and a chemical vapor deposition zone;

transporting a liquid precursor composition for said Group II metal-containing film to the vaporizer of the liquid delivery apparatus for vaporization of the precursor composition to yield a vapor-phase Group II metal precursor composition; and flowing the vapor-phase Group II metal precursor composition to the chemical vapor deposition zone for subsequent deposition of the Group II metal-containing film on the substrate therein, using a liquid precursor material comprising a tetrahydrofuran solution of a Group II metal p-diketonate adduct of the formula M(β-diketonate)$_2$(L)$_4$ wherein M is the Group II metal and L is tetrahydrofuran.

Another aspect of the invention relates to a liquid delivery process for forming a BST film on a substrate, comprising the steps of:

providing liquid precursors for each of the barium, strontium and titanium components of the BST film;

vaporizing each of the liquid precursors, separately or all together, to form the corresponding precursor vapor; and contacting the precursor vapor with a substrate to deposit barium, strontium and titanium thereon;

wherein the liquid precursors for barium and strontium comprise respective barium and strontium complexes in tetrahyrofuran solution, wherein each complex comprises a Group II metal β-diketonate adduct of the formula M(β-diketonate)$_2$(L)$_4$ wherein M is the Group II metal and L is tetrahydrofuran.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
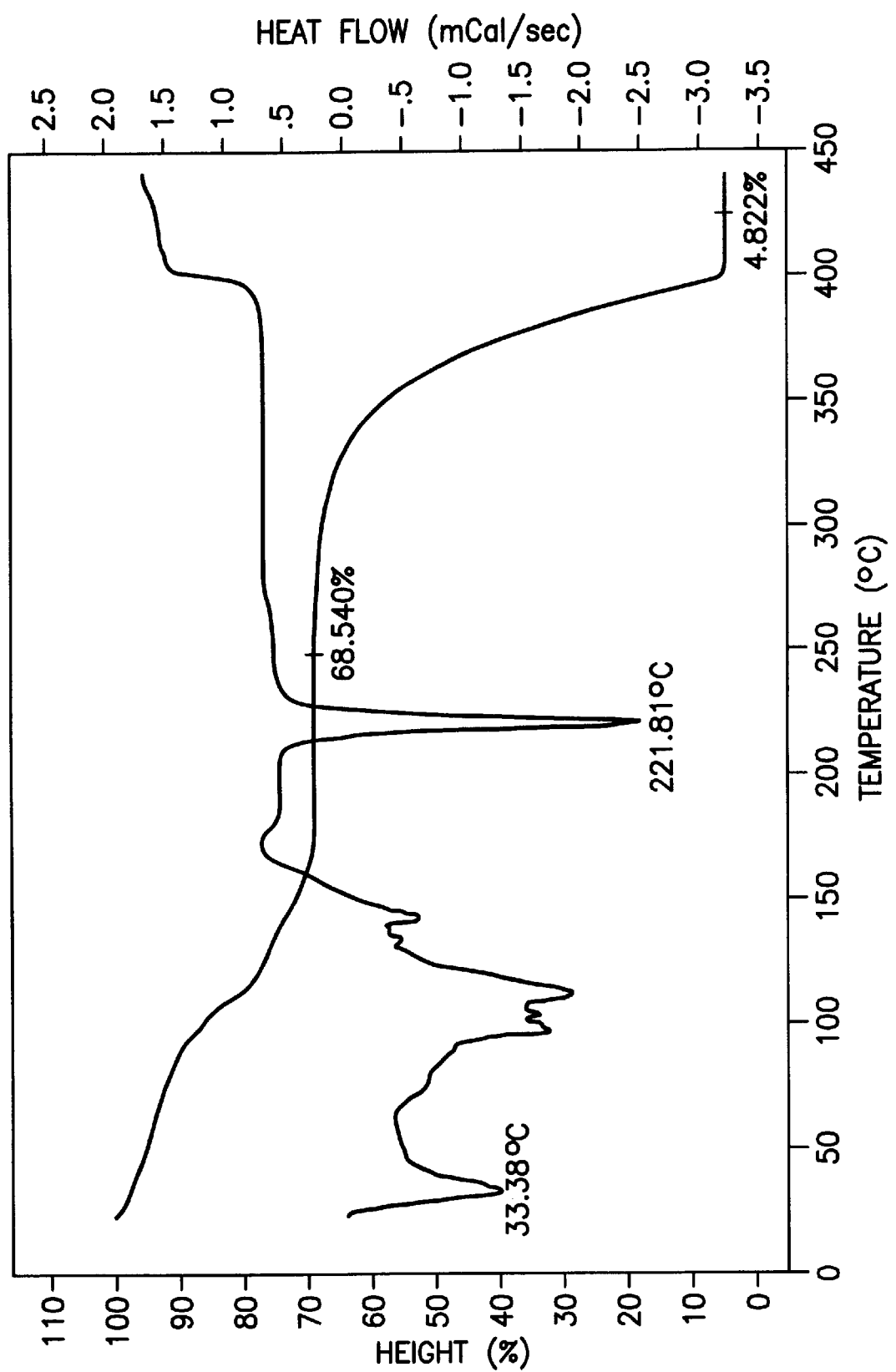
FIG. 1 is a composite thermogravimetric analysis (TGA) and differential scanning calorimetry (DSC) plot for Ba(thd)$_2$(THF)$_4$.

The present invention is based on the discovery of extremely high solubility of Group II β-diketonate complexes in tetrahydrofuran (THF) solvent and elucidation of a new composition of matter containing four THF ligands.

The unexpectedly high solubility of Group II β-diketonate complexes in tetrahydrofuran (THF) solvent is particularly surprising, given the solubility of corresponding Group II β-diketonate complexes in closely chemically related solvents such as tetrahydropyran (THP). Interestingly, the solubility maximum observed in tetrahydropyran (THP) is greatly reduced relative to THF, even though these two solvents are chemically similar.

The THF adducts of the present invention have the formula M(β-diketonate)$_2$(L)$_4$ where M is a Group II metal (Mg, Ca, Sr, Ba) and L is THF.

The β-diketonate ligand in such THF adducts may be of any suitable type. Illustrative species and their notational abbreviations include: acac=acetylacetonate, more specifically 2,4-pentanedionate; hfacac (or hfac)=hexafluoroacetylacetonate, more specifically 1,1,1,5,5,5-hexafluoro-2,4-pentanedionate; tfacac (or tfac)=trifluoroacetylacetonate, more specifically 1,1,1-rifluoro-2,4-pentanedionate; thd=tetramethylheptanedionate, and more specifically 2,2,6,6-tetramethyl-3,5-heptanedionate; fod=fluorodimethyloctanedionate, and more specifically 1,1,1,2,2,3,3-heptafluoro-7,7-dimethyl-4,6-octanedionate. The corresponding ketoiminate and β-thioketonate ligands may also be used and are identified consistently with the foregoing β-diketonate ligand notation, by prefixation of "n" and "s" to the corresponding β-diketonate ligand, e.g., nhfac, nthd, shfac, sthd, etc. Thus the β-diketonate ligands employed in metal source complexes of the present invention may usefully include acac, thd, fod, tfacac, and hfacac, and their corresponding nitrogen and thio analogs. Preferred THF adducts of the invention include Ba bis (2,2,6,6-tetramethyl-3,5-heptanedionate) and Sr bis (2,2,6,6-tetramethyl-3,5-heptanedionate).

In THF adducts of the present invention, the THF ligands stabilize the mononuclear form of the precursor, and satisfy the coordination requirements of the Group II center, thereby increasing the solubility and the volatility of the resultant complexes. While THF does not bind strongly and will readily dissociate upon heating or under vacuum from the complex, when the adduct of the invention is utilized in a solution of THF for liquid delivery chemical vapor deposition, the excess THF used as solvent effectively shifts the equilibrium to favor the THF adducted species of the invention. Such equilibrium shifts thereby limit the loss or liberation of THF from the complex, so that the complex remains storage stable in the liquid solution, but is readily volatilized and decomposed under chemical vapor deposition conditions in the reactor.

The THF adducting approach of the present invention overcomes the deficiencies of the prior art thermal stabilization approach of chelating the metal β-diketonate with ligands containing many donor atoms, such as crown ethers or lariat polyethers, to fulfill the coordination sphere. Such prior art thermal stabilization approach, while providing some improvement in stability relative to the metal β-diketonate per se, does not fully resolve the thermal stability issue. The precursor of the present invention overcomes this deficiency by providing a source reagent complex from which the THF ligands can be easily liberated under liquid delivery chemical vapor deposition conditions.

The THF adduct complexes of the invention may be readily obtained by cooling of THF solutions of the corresponding metal β-diketonate. The resulting solid complexes recovered from the THF solution are crystalline solids that have unusually low melting points and high solubilities in THF at room temperature (25° C.).

For example, the crystalline solid complexes recovered from solutions of $[Ba(thd)_2]_x$ and $[Sr(thd)_2]_x$ in THF, display unusually low melting points, 25° C. and 30° C., respectively. These values explain the relatively good vaporization behavior noted by liquid delivery "flash" vaporization. The high solubilities of $[Ba(thd)_2]_x$ and $[Sr(thd)_2]_x$ in THF at room temperature result from the formation of the THF coordination complexes shown in FIGS. 3 & 4. These low melting points as well as the crystalline appearance of the complexes evidence the compositions of the invention to be new mononuclear species comprising four THF ligands in the preferred molecular orientation.

The complexes of the present invention may be readily synthesized from the corresponding metal beta-diketonate compound $(M(\beta\text{-diketonate})_2)$ by dissolution of the metal β-diketonate compound in THF at ambient (room) temperature, with gentle stirring. The resulting complexes of the formula $M(\beta\text{-diketonate})_2(THF)_4$ may be recovered by evaporation, and recrystallization if desired, to yield the complex as a crystalline solid that is stable below its melting point. The complex may be furnished as a liquid or solid at the point of use, where it may be dissolved in THF to provide a suitable precursor solution for liquid delivery chemical vapor deposition applications. Such THF solution of the THF adduct complex may contain the complex at any suitable desired concentration, e.g., at a concentration of from about 10 to about 50% by weight of the THF adduct, based on the weight of the solution, for liquid delivery CVD usage. Concentrations expressed in molarity can range from 0.10M to >1.0M.

The liquid delivery CVD process using the THF adduct of the invention may be carried out at any suitable process conditions that are appropriate to the specific Group II metal-containing film being formed and to the end use of such film material, utilizing a suitable liquid delivery MOCVD system. Liquid delivery MOCVD systems may be employed of a type as more fully described in U.S. Pat. No. 5,204,314 issued Apr. 20, 1993 to Peter S. Kirlin et al. and U.S. Pat. No. 5,536,323 issued Jul. 16, 1996 to Peter S. Kirlin et al, and as commercialized under the trademark SPARTA by Advanced Technology Materials, Inc. (Danbury, Conn.). Other vaporizer designs including an aerosol vaporizer, acoustic transducer vaporizer or nebulizer may be used with good results.

The Group II metal in the complex may be barium, strontium, calcium, or magnesium. Precursor compositions may be formulated in the broad practice of the invention that comprise a mixture of different Group II metal complexes, wherein the Group II metals in the respective complexes are different from one another.

For example, a "cocktail" formulation of barium and strontium complexes may be employed for the MOCVD of a barium strontium titanate film on a substrate, where the Ba/Sr precursor formulation includes a precursor material of the present invention and a suitable Ti precursor for the titanium component of the film. The titanium source material may for example comprise a $Ti(O\text{-}iPr)_2(thd)_2$ source reagent in a solution including a solvent, such as for example a Lewis base ligand, tetrahydrofuran, or other compatible solvent species.

In the formation of the BST film, the respective source reagent materials in liquid form are vaporized in a vaporizer unit to form the precursor vapor. The vapor then is transported to the chemical vapor deposition reactor, containing a heated substrate, e.g., a wafer on a heated susceptor, that contacts the vapor to deposit the respective barium, strontium and titanium components in the desired stoichiometric relationship to one another.

The vapor may be delivered in the chemical vapor deposition chamber by a disperser such as a showerhead or nozzle, to provide a uniform flux of the vapor across the width of the wafer, to yield a correspondingly uniform thickness of deposited metal-containing film on the wafer. The process conditions (temperature, pressure, flow rate and composition of the vapor) may be suitably controlled to ensure an optimum process result for the MOCVD operation being conducted in the process system.

The deposition may be carried out in the presence of a suitable oxidant medium, to form the oxide film, or the metal film may after deposition of the respective Ba, Sr and Ti components be subjected to oxidation treatment to form the oxide film, within the skill of the art.

The Group II metal source reagent complexes of the invention have been characterized by thermal analysis techniques.

Figure 2:
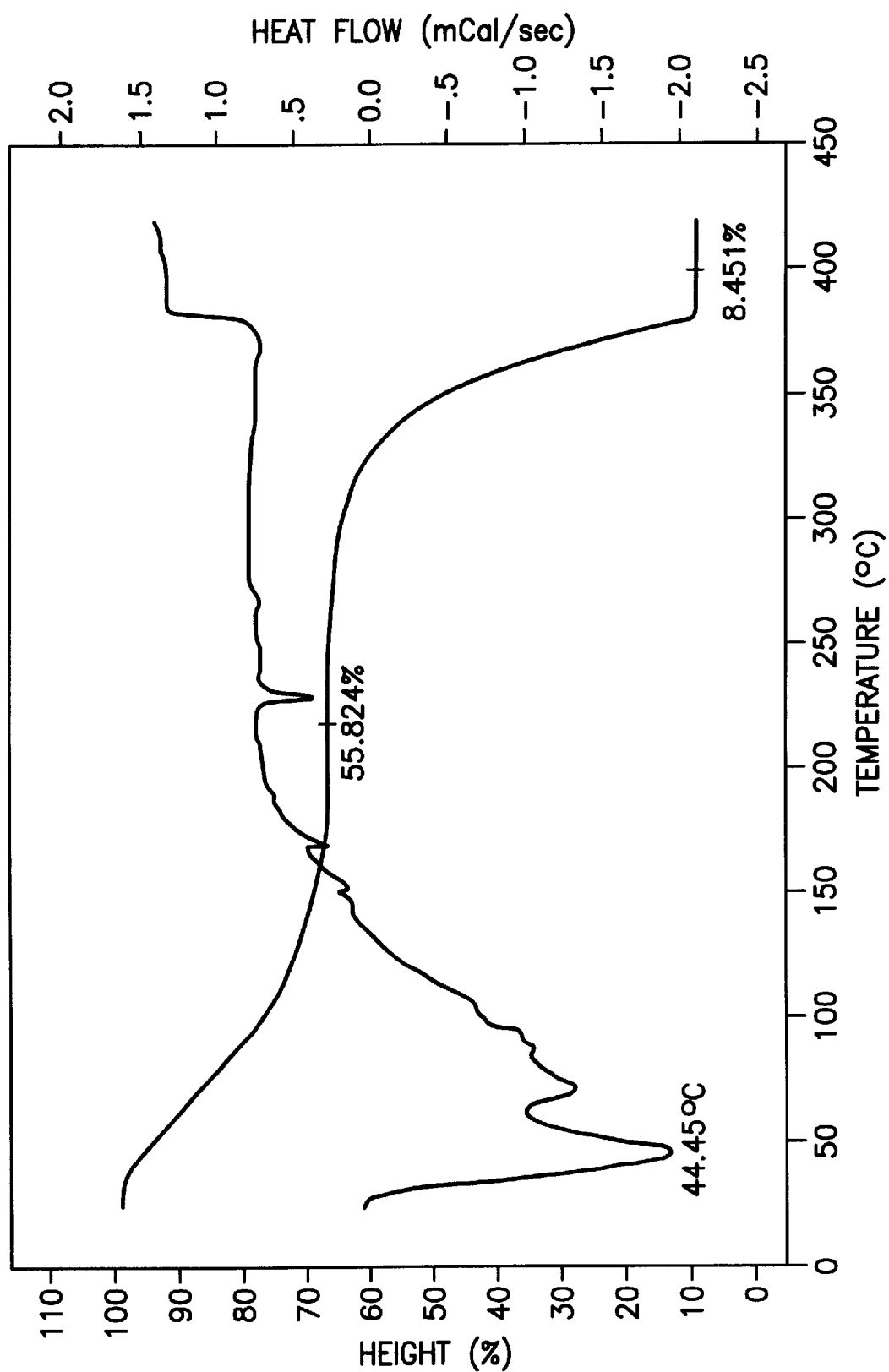
FIG. 2 is a composite thermogravimetric analysis (TGA) and differential scanning calorimetry (DSC) plot for Sr(thd)$_2$(THF)$_4$.

The results of standard thermal analysis (STA) comprising thermogravimetric analysis (TGA) and differential scanning calorimetry (DSC) is shown in FIG. 1 for $Ba(thd)_2(THF)_4$ and in FIG. 2 for $Sr(thd)_2(THF)_4$. These plots show that THF ligands dissociate easily from the complexes even at relatively low temperatures (<40° C.). The analyses also show that at least two THF ligands per metal atom are present in each case, and that such ligands are liberated below 150° C.

The data indicate that $[M(thd)_2]_x$ species are formed upon THF loss, as noted by the presence of characteristic melting point endothermic signals in each case. It is also noted that THF loss occurs even at room temperature under re-circulated nitrogen. Thus, the THF is loosely bound to the metal center.

The $^1H$ NMR spectrum of the Sr complex $Sr(thd)_2(L)_4$ in $C_6D_6$ shows somewhat broadened thd resonances at 5.9 and 1.28 ppm and only one set of THF resonances. Upon addition of excess THF, the thd resonances become sharper and no new THF resonances are seen. No significant changes in chemical shifts (>0.1 ppm) are observed. These observations suggest that THF ligands are liberated in solution and the system is dynamic, i.e., the rate of THF dissociation and re-coordination is fast relative to the NMR time-scale.

Figure 3:
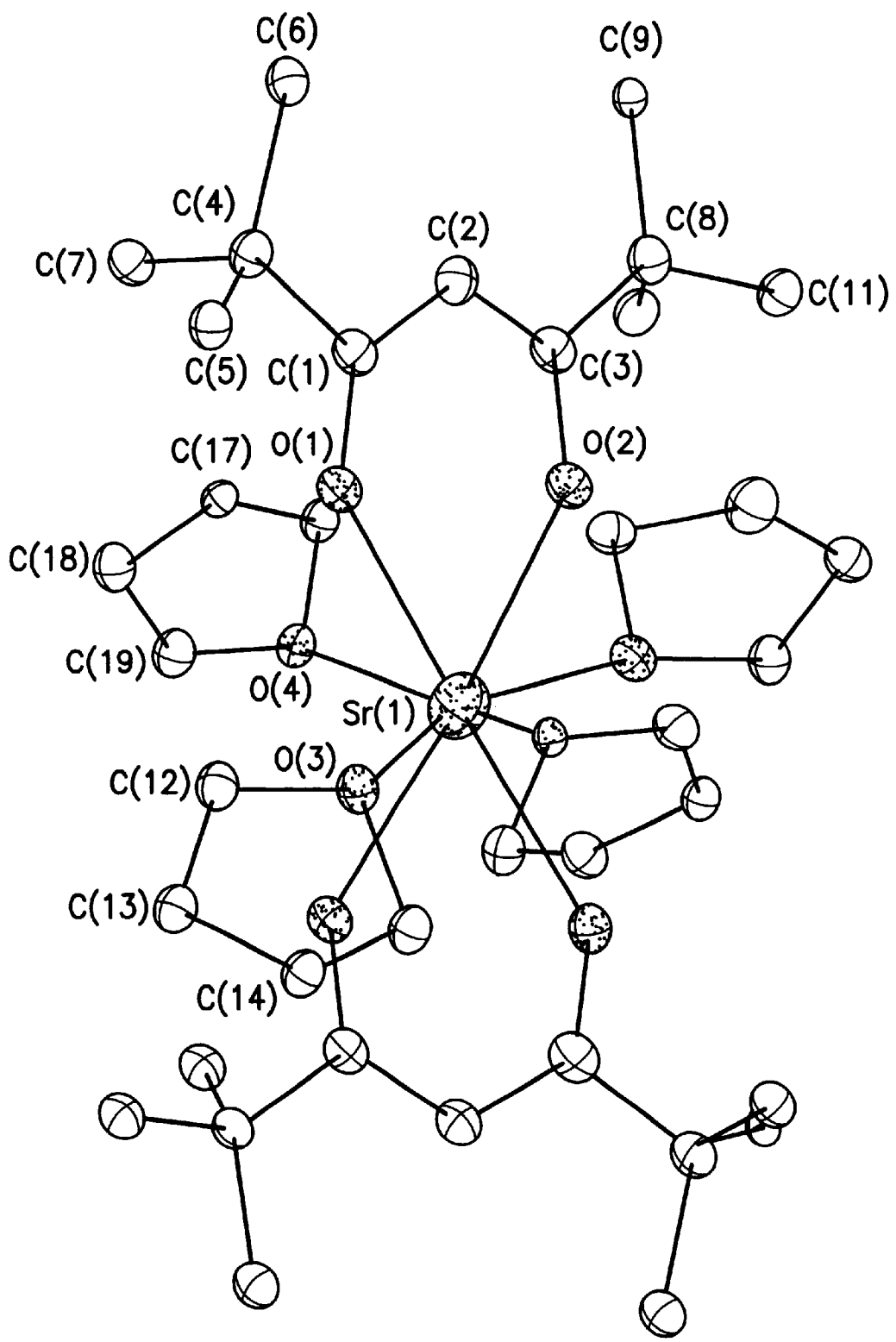
FIG. 3 is an ORTEP diagram of Sr(thd)$_2$(THF)$_4$ based on single crystal x-ray structural analysis.
Figure 4:
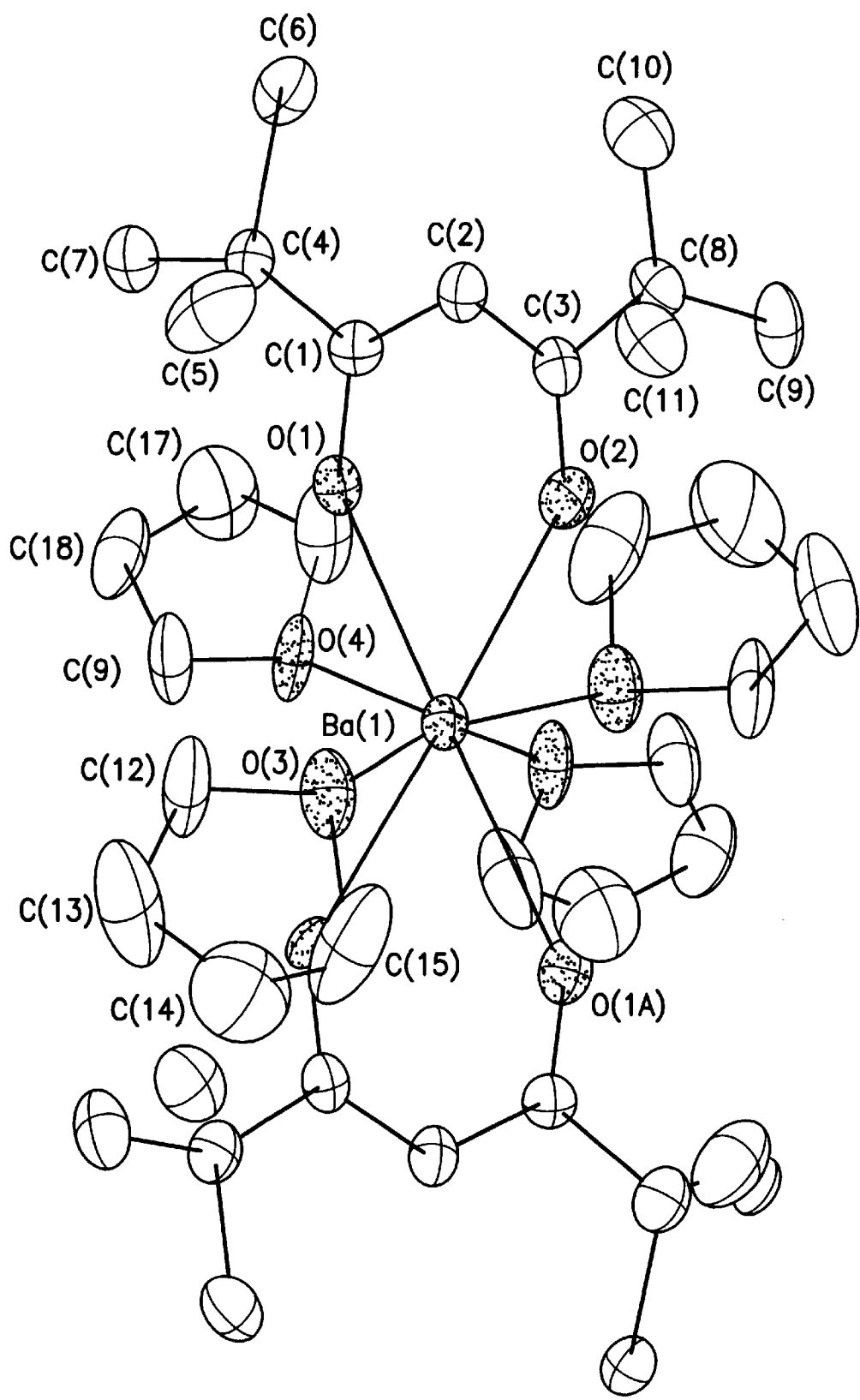
FIG. 4 is an ORTEP diagram of Ba(thd)$_2$(THF)$_4$ based on single crystal x-ray structural analysis.

X-ray structural determination of single crystal complexes of the present invention reveals that both complexes are mononuclear, containing four THF ligands positioned in the equatorial plane between the thd ligands (FIGS. 3=Ba(thd)$_2$(THF)$_4$; and FIG. 4=Sr(thd)$_2$(THF)$_4$). Apparently, the THF ligands can stabilize a mononuclear structure in these precursor complexes. Ba(thd)$_2$(THF)$_4$ displays a melting point of 25° C. and Sr(thd)$_2$(THF)$_4$ is observed to melt closer to 30° C. The low melting, single crystal precursor species of the invention are novel and unique, especially given the tendency of Ba(thd)$_2$ and Sr(thd)$_2$ to oligomerize and the reported chemical literature. The presence of excess THF during the liquid delivery and "flash" vaporization of the precursors of the invention achieves highly efficient vaporization of these materials.

Thus, the Group II metal source reagent solutions employed in the liquid delivery CVD process of the present invention may be readily employed for forming a Group II metal-containing film on a substrate, by the steps of volatilizing the Group II metal source reagent liquid solution to yield a Group II metal source vapor, and contacting the Group II metal source vapor with the substrate, to deposit the Group II metal-containing film thereon.

The various source reagent metal complexes employed in the practice of the invention may be readily made by conventional synthetic techniques, including those more fully described in U.S. Pat. No. 5,225,561, issued Jul. 6, 1993, the disclosure of which hereby is incorporated herein by reference.

The metal source reagent complex may readily be formulated into THF solution form, by conventional dissolution and solubilization techniques, for subsequent use as CVD source reagents having good shelf life characteristics and which are substantially stable in storage at ambient conditions (e.g., room temperature) as precursor solutions for MOCVD.

While the invention has been described herein with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the invention.

What is claimed is:

1. A method of forming a Group II metal-containing film on a substrate, comprising the steps of:

providing a liquid delivery apparatus including a vaporizer and a chemical vapor deposition zone;

transporting a Group II metal, liquid precursor composition for said Group II metal-containing film to the vaporizer of the liquid delivery apparatus for vaporization of the Group II metal, liquid precursor composition to yield a vapor-phase Group II metal precursor composition; and flowing the vapor-phase Group II metal precursor composition to the chemical vapor deposition zone for subsequent deposition of the Group II metal-containing film on the substrate therein, wherein said Group II metal, liquid precursor material composition comprises a tetrahydrofuran solution of a Group II metal β-diketonate adduct of the formula M(β-diketonate)$_2$(L)$_4$ wherein M is the Group II metal and L is tetrahydrofuran.

2. The method of claim 1 wherein the concentration of the adduct in the solution is from about 10% to about 50% by weight, based on the total weight of the solution.

3. The method of claim 1 wherein M is barium.

4. The method of claim 1 wherein M is strontium.

5. The method of claim 1 including barium and strontium adducts.

6. The method of claim 1 wherein M is barium and the adduct has a melting point of about 25° C.

7. The method of claim 1 wherein M is strontium and the adduct has a melting point of about 30° C.

8. The method of claim 1 wherein the adduct has the ORTEP diagram structure illustrated in FIG. 3 hereof.

9. The method of claim 1 wherein the adduct has the ORTEP diagram structure illustrated in FIG. 4 hereof.

10. The method according to claim 1, wherein the Group II metal-containing film comprises BST.

11. The method according to claim 10, wherein the titanium component of the BST film, is deposited from a liquid precursor composition comprising Ti(O-iPr)$_2$(thd)$_2$.

12. A liquid delivery process for forming a BST film on a substrate, comprising the steps of:

providing liquid precursors for each of the barium, strontium and titanium components of the BST film;

vaporizing the barium, strontium and titanium liquid precursors, to form a corresponding multi-component precursor vapor; and contacting the multi-component precursor vapor with a substrate to deposit barium, strontium and titanium thereon;

wherein said liquid precursors for barium and strontium each comprise a metal β-diketonate adduct dissolved in tetrahydrofuran, said metal β-diketonates having a formula M(β-diketonate)$_2$(L)$_4$ wherein M is barium or strontium and L is tetrahydrofuran.

\* \* \* \* \*